(12) United States Patent
Wei

(10) Patent No.: US 9,342,657 B2
(45) Date of Patent: May 17, 2016

(54) METHODS FOR PREDICTING AN INDIVIDUAL'S CLINICAL TREATMENT OUTCOME FROM SAMPLING A GROUP OF PATIENT'S BIOLOGICAL PROFILES

(76) Inventor: Nien-Chih Wei, Warren, NJ (US)

(*) Notice: Subject to any disclaimer, the term of this patent is extended or adjusted under 35 U.S.C. 154(b) by 2031 days.

(21) Appl. No.: 10/394,137

(22) Filed: Mar. 24, 2003

(65) Prior Publication Data

US 2004/0193019 A1 Sep. 30, 2004

(51) Int. Cl.
| | |
|---|---|
| G01N 33/48 | (2006.01) |
| G01N 33/50 | (2006.01) |
| G06F 19/00 | (2011.01) |
| G06F 19/18 | (2011.01) |
| G06F 19/12 | (2011.01) |
| G06F 19/20 | (2011.01) |
| G06F 19/24 | (2011.01) |

(52) U.S. Cl.
CPC ........... *G06F 19/3443* (2013.01); *G06F 19/18* (2013.01); *G06F 19/3437* (2013.01); *G06F 19/12* (2013.01); *G06F 19/20* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 5,674,872 A * | 10/1997 | Johnson | 514/283 |
| 5,769,074 A * | 6/1998 | Barnhill et al. | 600/300 |
| 6,222,093 B1 | 4/2001 | Marton et al. | 800/3 |
| 6,223,074 B1 | 4/2001 | Granger | 600/544 |
| 6,245,511 B1 | 6/2001 | Gulati | 435/6 |
| 6,280,393 B1 | 8/2001 | Granger et al. | 600/544 |
| 6,461,807 B1 | 10/2002 | Friend et al. | 435/4 |
| 6,463,321 B2 | 10/2002 | Granger | 600/544 |
| 6,466,816 B2 | 10/2002 | Granger et al. | 600/544 |
| 6,871,171 B1 | 3/2005 | Agur et al. | |
| 6,949,342 B2* | 9/2005 | Golub et al. | 435/6 |
| 7,133,814 B2 | 11/2006 | Agur et al. | |
| 7,266,483 B2 | 9/2007 | Agur et al. | |
| 2001/0044431 A1* | 11/2001 | Rodriguez | 514/179 |
| 2002/0006616 A1* | 1/2002 | Gish et al. | 435/6 |
| 2002/0069087 A1* | 6/2002 | Fairley et al. | 705/2 |
| 2002/0095260 A1* | 7/2002 | Huyn | 702/19 |
| 2003/0049701 A1* | 3/2003 | Muraca | 435/7.23 |
| 2003/0158829 A1* | 8/2003 | Kam | 706/15 |
| 2004/0018528 A1* | 1/2004 | Morimoto et al. | 435/6 |

FOREIGN PATENT DOCUMENTS

WO WO 01/31580 A2 * 5/2001

OTHER PUBLICATIONS

Haybittle et al. A prognostic index in primary breast cancer. British Journal of Cancer. 1982, vol. 45, pp. 361-366.*
Todd et al. Confirmation of a prognostic index in primary breast cancer. British Journal of Cancer. vol. 56, pp. 489-492.*
Comer et al. Sertraline: A review of its therapeutic use in post-traumatic stress disorder. CNS Drugs. 2000, vol. 14, pp. 391-407.*
Furey et al. Support vector machine classification and validation of cancer tissue damples using microarray expression data. Bioinformatics. 2000, vol. 16, pp. 906-914.*
Wolberg et al. Computerized breast cancer diagnosis and prognosis from fine-needle aspirates. Archives of Surgery. 1995, vol. 130, pp. 511-516.*
CLIP Investigators. A new prognostic system for hepatocellular carcinoma: a retrospective study of 435 patients. Hepatology, 1998, vol. 28, pp. 751-755.*
Lopez et al. A phase I trial of AUC-directed carboplatin with infusional doxorubicin and ifosfamide plus G-CSF is patients with advanced gynecologic malignancies. Cancer Chemotherapy and Pharmacology, 2000, vol. 46, pp. 411-415.*
Singh et al. Gene expression correlates of clinical prostate cancer behavior. Cancer Cell, Mar. 1, 2002, vol. 1, pp. 203-209.*
Ramaswamy et al. Multiclass cancer diiagnosis using tumor gene expression signatures. PNAS, 2001, vol. 98, pp. 15149-15154.*
Abrams et al. Cancer Journal from Scientific American, 1998, vol. 4, p. 178. printed 11 pages from online source.*
Okuda et al. Cancer, vol. 56, 1985, pp. 918-928.*
Stewart et al. Role of genetic factors in the pathogenesis of osteoporosis. Journal of Endocrinology, 2000, vol. 166, pp. 235-245.*
Takahashi et al. Expression of vascular endothelial growth factor and its receptor, KDR, correlates with vascularity, metastasis, and proliferation of human colon cancer. Cancer Research, 1995, vol. 55, pp. 3964-3968.*
Polissar et al. Time trends and key factors in the choice of one-step or two-step biopsy and surgery for breast cancer. Social Science & Medicine, 1985, vol. 21, pp. 733-740.*
Boyer et al. Microsatellite instability, mismatch repair deficiency, and genetic defects in human cancer cell lines. Cancer Research, 1995, vol. 55, pp. 6063-6070.*
Definition of RTOG. Obtained online on Mar. 12, 2010 << http://www.acr.org/SecondaryMainMenuCategories/ClinicalResearch/RadiationTherapyOncologyGroupRTOG.aspx >>.*
Farinati, F., et al., "How Should Patients with Hepatocellular Carcinoma be Staged? Validation of a New Prognostic System," Cancer, American Cancer Society, Dec. 1, 2000, vol. 89, No. 11, United States of America.

(Continued)

Primary Examiner — Russell S Negin
(74) Attorney, Agent, or Firm — Nevrivy Patent Law Group P.L.L.C.

(57) ABSTRACT

Methods, systems, and computer program products that predict an individual's treatment outcome from a sampling of a group of patients' biological profiles. Biological profile information is received from patients who had a medical condition and who received a treatment. Treatment outcome information regarding the patients who had the medical condition and who received the treatment is also received. A discriminant analysis-based pattern recognition process is then performed on the biological profile information and the treatment outcome information, thereby generating a model that correlates between the biological profile information and the treatment outcome information. The model can be used for, among other things, predicting treatment outcome for the new patient for the treatment.

54 Claims, 7 Drawing Sheets

(56) References Cited

OTHER PUBLICATIONS

"FDA Talk Paper: FDA Approves Camptosar for First Line Therapy in Treatment of Advanced Colorectal Cancer," United States Department of Health and Human Services, Food and Drug Administration, Apr. 20, 2000, T00-18, http://www.fds.gov/bbs/topics/ANSWERS/ANS01011.html.

Guglielmi, Alessandra P., et al., "Second-Line Therapy for Advanced Colorectal Cancer", Gastrointestinal Cancer Research, vol. 1, Issue 2, International Society of Gastrointestinal Oncology, Mar./Apr. 2007, p. 57-63.

Pusztai, Lajos, et al., "Individualized Chemotherapy Treatment for Breast Cancer: Is it Necessary? Is it Feasible?", Drug Resistance Updates, vol. 7, Elsevier Press 2004, p. 325-331.

Thatcher, Nicholas, "First- and Second-Line Treatment of Advanced Metastatic Non-Small-Cell Lung Cancer: A Global View", BMC Proceedings 2008, 2(Suppl 2): S3, BioMed Central, http://biomedcentral.com/1753-6561/2/S2/S3 Sep. 24, 2008, p. 1-6.

Tuma, Rabiya S., "Using Molecular Information for Prognosis and Treatment Choice", Oncology Times, vol. 29, No. 10, NY, New York May 25, 2007, p. 51-52.

U.S. FDA, "Critical Path to Personalized Medicine", Office of Management Budget Formulation and Presentation, http://www.fda.gov/oc/oms/ofm/budget/2007/HTML/4CPPOM1.htm 2007, p. 1-3.

Steineck, et al., "Distinguishing prognostic and treatment predictive information for localized prostate cancer" Urology, Apr. 1995, vol. 45, No. 4, pp. 610-615.

Adolfsson, et al., "Prognostic and treatment predictive factors—is there a difference?", Prostate Cancer and Prostatic Diseases, 2000, vol. 3, pp. 265-268.

Cianfrocca, et al., "Prognostic and Predictive Factors in Early-Stage Breast Cancer", The Oncologist, 2004, vol. 9, pp. 606-616.

Mori, et al., "Predictive and prognostic markers for invasive breast cancer", Pathology International, 2002, vol. 52, pp. 186-194.

Tejpar, et al., "Prognostic and Predictive Biomarkers in Resected Colon Cancer: Current Status and Future Perspectives for Integrating Genomics into Biomarker Discovery", The Oncologist, 2010, vol. 15, pp. 390-404.

Oldenhuis, et al., "Prognostic versus predictive value of biomarkers in oncology", European Journal of Cancer, 2008, vol. 44, pp. 946-953.

Van'T Veer, et al., "Gene expression profiling predicts clinical outcome of breast cancer", Nature, Jan. 31, 2002, vol. 415, pp. 530-536.

Van De Vijver, et al., "A gene expression signature as a predictor of survival in breast cancer", New England Journal of Medicine, Dec. 19, 2002, vol. 347, No. 25, pp. 1999-2009.

"First Line Therapy (Code C45792)", National Cancer Institute, http://ncit.nci.nih.gov/ncitbrowser/ConceptReport.jsp?dictionary=NCI%20Thesaurus&code=C45792, accessed web site on Mar. 30, 2014.

"Combination Drug Therapy (Code C16144)", National Cancer Institute, http://ncit.nci.nih.gov/pp./concept_details.jsf?dictionary=NCI%20Thesaurus&code=C16144, accessed web site on Mar. 30, 2014.

"Disease Predictive Factor (Code C28282)", National Cancer Institute, http://ncit.nci.nih.gov/ncitbrowser/ConceptReport.jsp?dictionary=NCI%20Thesaurus&code=C28282, accessed web site on Mar. 30, 2014.

"Prognostic Factor (Code C18959)", National Cancer Institute, http://ncit.nci.nih.gov/ncitbrowser/ConceptReport.jsp?dictionary=NCI%20Thesaurus&code=C18959, accessed web site on Mar. 30, 2014.

"Second Line Treatment (Code C54350)", National Cancer Institute, http://ncit.nci.nih.gov/ncitbrowser/ConceptReport.jsp?dictionary=NCI%20Thesaurus&code=C54350, accessed web site on Mar. 30, 2014.

Brünner, :What is the Difference Between 'Predictive and Prognostic Biomarkers'? Can you Give Some Examples?, Connection, 2009, pp. 18.

Draft Guidance for Industry, Clinical Laboratories, and FDA Staff, In Vitro Diagnostic Multivariate Index Assays, U.S. Food and Drug Administration, Jul. 26, 2007.

Lin, Daniel W., et al., "Influence of Surgical Manipulation on Prostate Gene Expression: Implications for Molecular Correlates of Treatment Effects and Disease Prognosis," Journal of Clinical Oncology, 24(23):3763-3770 (2006).

National Cancer Institute Thesarus, Prognostic Factor (Code C18959), http://ncit.nci.nih.gov/ncitbrowser/ConceptReport.jsp?dictionary=NCI%20Thesaurus&code=C18959 (last visited May 21, 2015).

National Cancer Institute Thesarus, Disease Predictive Factor (Code C28282), http://ncit.nci.nih.gov/ncitbrowser/ConceptReport.jsp?dictionary=NCI%20Thesaurus&code=C28282 (last visited May 21, 2015).

National Cancer Institute Thesarus, Combination Drug Therapy (Code C16144), http://ncit.nci.nih.gov/pages/concept_details.jsf?dictionary=NCI%20Thesaurus&code=C16144 (last visited May 21, 2015).

National Cancer Institute Thesarus, First-Line Therapy (Code C45792), http://ncit.nci.nih.gov/ncitbrowser/ConceptReport.jsp?dictionary=NCI%20Thesaurus&code=C45792 (last visited May 21, 2015).

National Cancer Institute Thesarus, Second Line Treatment (Code C54350), http://ncit.nci.nih.gov/ncitbrowser/ConceptReport.jsp?dictionary=NCI%20Thesaurus&code=C54350 (last visited May 21, 2015).

Zhang et al., Intratumor heterogeneity in localized lung adenocarcinomas delineated by multiregion sequencing, Science, 346:256-259 (2014).

Gerlinger et al., Intratumor Heterogeneity and Branched Evolution Revealed by Multiregion Sequencing, The New England Journal of Medicine, 366:883-892 (2012).

* cited by examiner

Figure 2 An example of a separated gene distribution.

Figure 3 A custom-made staple gun for pulverizing frozen tissue.

Figure 4 RNA examined by gel electrophoresis.

Figure 5 Image produced by scanning microarray.

Figure 6 Discriminant analysis of response to radiotherapy.

METHODS FOR PREDICTING AN INDIVIDUAL'S CLINICAL TREATMENT OUTCOME FROM SAMPLING A GROUP OF PATIENT'S BIOLOGICAL PROFILES

FIELD OF INVENTION

The present invention is directed to methods, systems, and computer program products that predict an individual's treatment outcome from a sampling of a group of patients' biological profiles.

BACKGROUND

It is well known that drug response varies greatly among different people with respect to efficacy and side effects experienced. For example, aspirin causes gastrointestinal distress in some users; certain antihistamine drugs are not beneficial for all. This population variability can also be seen in the treatment of serious and lethal diseases such as cancer. A patient will begin a treatment, and, depending on the efficacy and side effects, the clinician will decide if he/she should continue the treatment or switch to another regimen.

When treating certain serious diseases, this try-and-switch method can have severe consequences; this is particularly true in the time-sensitive case of cancer treatment. One does not know the efficacy of different chemotherapies for an individual, thus making it difficult to design an effective treatment plan; the outcomes of their treatments are essentially random. As most cancer patients will receive chemotherapy during the course of their disease, many will suffer from the treatment's ineffectiveness and experience possible side effects to their already fragile health.

This situation is a result of the limited scope in current clinical trial design. These trials are designed to determine drug efficacy across a patient population. The results of the trials represent the statistical probability of effectiveness for a group of patients. There is no specific information about the drug's efficacy for an individual patient.

Conventional In Vitro and In Vivo Drug Efficacy Assays

For many years, drug efficacy prediction has been determined using in vitro and in vivo assays, which are designed to measure the response of tumors to drugs in a simulated environment. Although many assays are highly sophisticated with careful experimental design and excellent technique, there are basic limitations to these approaches. Furthermore, most clinicians question the validity of these experiments.

Generally, in vitro chemosensitivity assays are used for predicting patient response to drug therapy. Primary cancerous or metastatic cells are isolated from tumors and incubated with chemotherapeutic drugs. Cell survival is then assessed, and results are interpreted to determine a patient's tumor sensitivity or resistance to the drugs. There are many problems with these experiments. First, there are issues independent of the assay used, which include the differences between primary versus metastatic cells, the choice of drug concentrations, and heterogeneity in tumor specimens. Secondly, there are assay-specific issues such as the inability to distinguish between the growth of malignant and nonmalignant cells in culture. Thirdly, there are technical difficulties with the human tumor cloning assay, where about half of the specimens do not experience growth; as a result, colonies are unavailable for quantification in a drug response readout. In addition to the above deficiencies, these experiments may have other issues; for example, the requirement of long incubation time (14 to 28 days) for the assay is impractical for use in clinical practice. Furthermore, there are significant differences between in vitro assay conditions and in vivo physiological environments, thereby rendering doubts in the validity of the drug response observed in vitro and its potential clinical application.

One alternative to the in vitro experiments has been the extreme drug resistance study (EDR), which focuses on drug resistance rather than drug sensitivity. In these experiments, the tumors are treated with very high drug concentrations for a long exposure time. The hypothesis is that if the tumors fail to exhibit response under these extreme conditions the patient will also be unresponsive to the drug. Kern and Weisenthal first reported positive EDR results (See, Kern, D. H., Weisenthal, L. M., "Highly specific prediction of antineoplastic drug resistance with an in vitro assay using suprapharmacologic drug exposures," (1990) J Natl Cancer Inst; 7:582), incorporated herein by reference in its entirety, but they could not be confirmed by others in subsequent studies. In a study of patients with stage II ovarian cancer, no difference in 3-year survival rate was predicted by the EDR assay. (See, Orr, J. W. Jr, Orr, P, Kern, D. H., Cost-effective treatment of women with advanced ovarian cancer by cytoreductive surgery and chemotherapy directed by an in vitro assay for drug resistance, (1999) Cancer J Sci Am 5:174-178, incorporated herein by reference in its entirety). In another study by Eltabbakh (See, Eltabbakh, G. H., Piver, M. S., Hempling, R. E., et al. "Correlation between extreme drug resistance assay and response to primary paclitaxel and cisplatin in patients with epithelial ovarian cancer," (1998) Gynecol Oncol; 70:392-397, incorporated herein by reference in its entirety), on 75 ovarian cancer patients, the EDR assay also failed to demonstrate any advantage in predicting drug response. A prospective study on 95 colorectal and appendiceal cancer patients also failed to correlate sensitivity or resistance of tumors with the in vitro prediction assay. (See, "Fernandez-Trigo, V., Shansa, F., Vidal-Jove, J., et al. Prognostic implications of chemoresistance-sensitivity assays for colorectal and apendiceal cancer," (1995) Am J Clin Oncol; 18:454-460, incorporated herein by reference in its entirety).

An improvement to the in vitro approach is the in vivo technique, which studies the three-dimensional cell structure of tumors, as well as the metabolic, activational effects of the drug. In vivo experiments typically utilize immune-deficient mice by implanting tumor cells under the subrenal capsule or inoculating the animals with cancer cells. Some promising results were reported for the former. (See, for example, Bogden, A. E., "The subrenal capsule assay and its predictive value in oncology," (1985) Ann Chir Gynaecol; 74 (suppl 199):12), incorporated herein by reference in its entirety). While in vivo experimentation is designed to closely mimic the complexities of the biological system, there are still many factors that cannot be duplicated through animal modeling. For example, the mouse's drug metabolism and host toxicity may not be comparable to that in the human, or the tumors introduced could behave differently than the tumors in the human system. (See Cunningham, D. et al, "The 6-day subrenal capsule assay is of no value with primary surgical explants from gastric cancer," (1986) Br. J Cancer; 54:519, incorporated herein by reference in its entirety). In addition, the significant duration of time needed in these experiments makes it difficult to use these assays for diagnostic purposes. Often, an in vivo experiment can take up to three months before results are obtained, which is acceptable in cancer research, but highly unlikely to be applicable in clinical practice.

In summary, both in vivo and in vitro experimental techniques for predicting individual patient drug response have inherent problems. Most obvious are the differences imposed by the experimental system, which are in contrast to the physiological environment in a patient. Also, disparity in tumor types, levels of drug concentration, and issues of quality control can prove to be problematic in these in vitro predictive tests.

Recent Status of Pharmacogenetics

Because many diseases are genetic disorders, gene expression is expected to be able to predict their response to treatment. There are a few cases of a single marker gene being linked to chemotherapeutic efficacy. For example, in treatment of breast cancer, Tamoxifen is used in ER-positive tumors, and Herceptin is used when the growth factor receptor HER2 is overexpressed. However, these are exceptions; generally, one cannot expect a single marker gene to reliably predict a drug's effectiveness. Instead, many genes related to drug response need to be identified. Subsequent development of an optimal method for combining the information from these genes is required. This new approach affects a long list of diseases related to genetic disorder as reported by NIH: Cancer, Blood and Lymph Diseases, The Digestive System, Ear Nose and Throat, Diseases of the Eye, Female-Specific Diseases, Glands and Hormones, The Heart and Blood Vessels, Diseases of the Immune System, Male-Specific Diseases, Muscle and Bone, Neonatal Diseases, The Nervous System, Nutritional and Metabolic Diseases, Respiratory Diseases, Skin and Connective Tissue. (See,"Genes and Disease", by National Center for Biotechnology Information," incorporated herein by reference in its entirety.) The goal of pharmacogenetics is to understand the genetic disorder; the results would provide a better predictive model than that of a single marker gene.

The recent advent of DNA microarray, or gene chip technology, provides a platform for potentially analyzing all human genes in a single experiment. This technique has revolutionized pharmacological investigations (See, Lander, E. S. et al., "Initial sequencing and analysis of the human genome. Nature 409:860-921, (2001); and Venter, J. C. et al., "The sequence of the human genome. Science," 291:1304-1351, (2001); incorporated herein by reference in their entireties.) Monitoring gene expression profiles can provide insight into the molecular fingerprint of diseases. This technique also provides a basis for studying therapeutic treatments, environmental agents, and can ultimately help in distinguishing between responders and non-responders to a given drug, as well as predicting toxicity and other adverse effects on the basis of altered patterns in expression profiles.

As of yet, clinical gene-based cancer research is very limited. Some have used microarrays to infer differences between normal and cancerous tissues (See, Welsh, J. B., et al., "Analysis of Gene Expression Profiles in Normal and Neoplastic Ovarian Tissue Samples Identifies Candidate Molecular Markers of Epithelial Ovarian Cancer," Proc. Natl. Acad. Sci. USA 98, 1176-1181, (2001); and Alon, U., et al., "Broad Patterns of Gene expression revealed by clustering analysis of tumor and normal colon tissues probed by oligonucleotide arrays," Proc. Natl. Acad. Sci. USA, 96, 6745-6750, (1999); incorprated herein by reference in their entireties.) These studies were designed to find marker genes or co-regulated genes. Another application for microarray study has been the molecular classification of cancer tissues using their pathological characteristics (e.g. metastatic, invasive, or AML vs. ALL in leukemia). These studies have been successful in separating breast, melanoma, leukemia, lung, and lymphoma tissues according to their genetic profiles (See Laura J. van't Veer, Hongyue Dai, et al., "Gene expression profiling predicts clinical outcome of breast cancer, Nature, 415, 530-536 (2002); Marc J. van de Vijver, et al., "A gene expression signature as a predictor of survival in breast cancer," N Engl J Med, 347, No. 25, 1999-2009 (2002); Bittner, M., et al., "Molecular classification of cutaneous malignant melanoma by gene expression profiling," Nature 406, 536-540 (2000); Golub, T. R., et al., "Molecular Classification of Cancer: Class Discovery and Class Prediction by Gene Expression Monitoring," Science, 286, 531-537 (1999); Bhattacharjee, A., et al., "Classification of human lung carcinomas by mRNA expression profiling reveals distinct adenocarcinoma subclasses," Proc. Natl. Acad. Sci. USA 98, 13790-13795 (2001); and Alizadeh, Ash A., et al., "Distinct Types of Diffuse Large B-Cell Lymphoma Identified by Gene Expression Profiling," Nature, 403, 503-511 (2000); incorporated herein by reference in their entireties.)

However, none of these studies address the predictability of treatment outcome.

Current Research Status on Predicting Treatment Outcome

Drug resistance in cancer treatment is an especially critical problem. Genomics approaches, such as the use of DNA microarrays, have been used to identify genetic pathways that contribute to drug resistance in cancer. As this approach requires detailed analysis of many individual pathways, it is still far from gaining a comprehensive understanding of the complex relationships among genomic, molecular, cellular, and clinical phenotypes.

Because there is very limited knowledge of genetic pathways in clinical application, DNA microarray analysis has been utilized for studying drug response in in vitro and in vivo environments. Studies have been reported relating genome-wide gene expression from changes in response to chemotherapeutic agents to tumor tissue drug response directly without having to specify the pathway of analysis. (See Staunton, J. E., et al., "Chemosensitivity prediction by transcriptional profiling," Proc. Natl. Acad. Sci. USA 98, 10787-10792 (2001); Zembutsu, H., et al., "Genome-wide cDNA microarray screening to correlate gene expression profiles with sensitivity of 85 human cancer xenografts to anticancer drugs," Cancer Res. 62:518-527 (2002); incorporated herein by reference in their entireties). Due to the limitations of the experimental design, these results were not definitive enough to determine if a sample's gene profile could be accurately related to a specific drug response. However, even if further in vitro or in vivo studies had provided positive results, direct clinical application still would not have been possible.

What are needed are methods, systems, and computer program products that predict an individual's treatment outcome from a sampling of a group of patients' biological profiles.

SUMMARY OF THE INVENTION

The present invention is directed to methods, systems, and computer program products that predict an individual's treatment outcome from a sampling of a group of patients' biological profiles.

In accordance with an aspect of the invention, biological profile information is received from patients who were diagnosed with a medical condition and who received a treatment. Treatment outcome information regarding the patients who had the medical condition and who received the treatment is also received. A discriminant analysis-based pattern recognition process is then performed on the biological profile information and the treatment outcome information, thereby generating a model that correlates between the biological profile information and the treatment outcome information. The model can be used for, among other things, predicting treatment outcome for the new patient for the treatment. These and other features of the invention are described herein.

BRIEF DESCRIPTIONS OF FIGURES

The present invention will be described with reference to the accompanying drawings, wherein like reference numbers indicate identical or functionally similar elements. Also, the leftmost digit(s) of the reference numbers identify the drawings in which the associated elements are first introduced.

DETAILED DESCRIPTIONS OF THE INVENTION

Table of Contents

Figure 1:
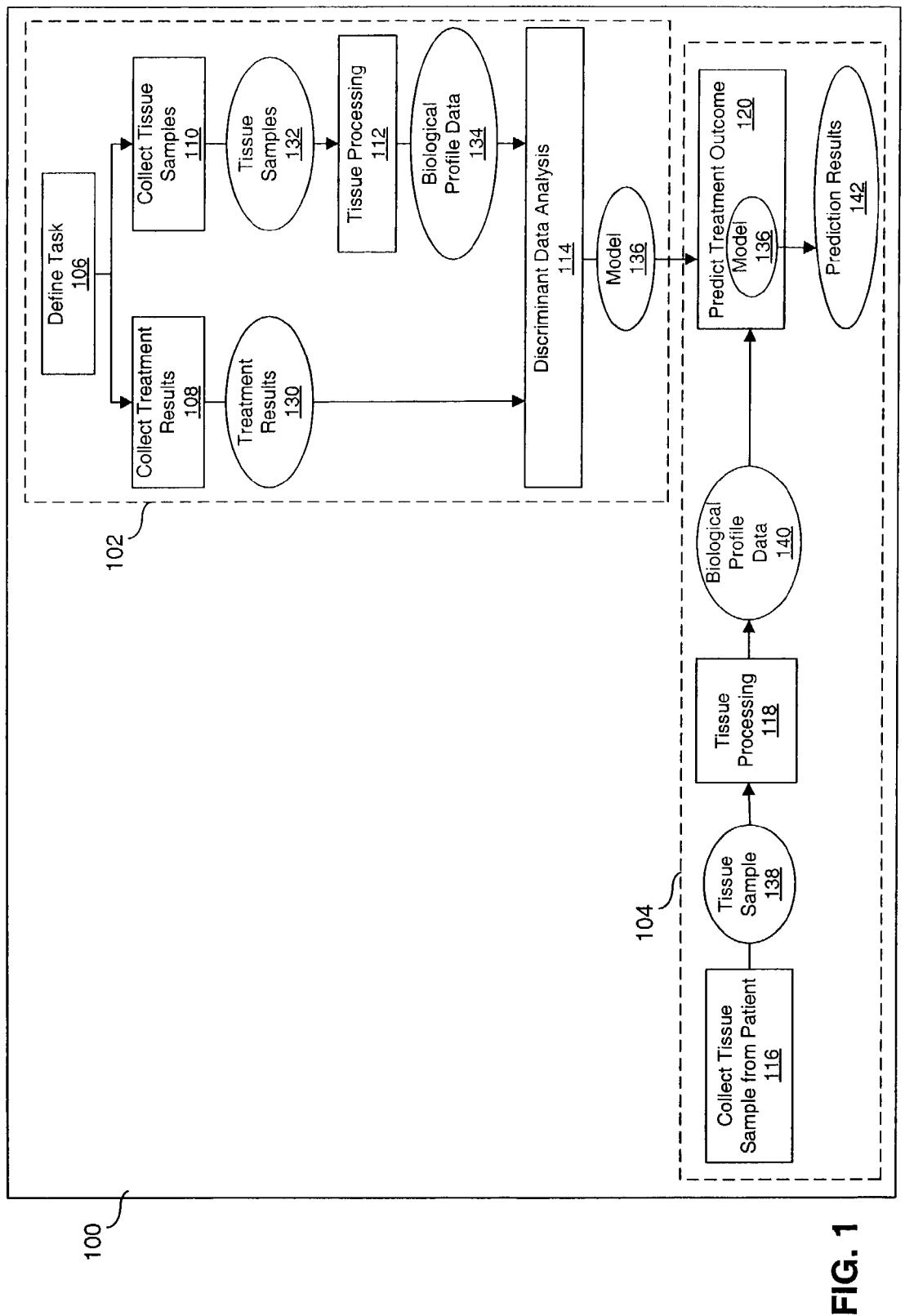
FIG. 1 is an example process flowchart for generating and using a model to predict an individual's treatment outcome from a sampling of a group of patients' biological profiles.

I. Introduction
II. A Process for Predicting Treatment Outcome
III. Example Commercial Applications
IV. Comparisons with Other Approaches on the Prediction of Treatment Outcome
   A. Top-Down Approach Versus Conventional Bottom-Up Approach
   B. Sample Patient to Form Prediction Model
V. Biological Profiles
   A. Use a patient's non-targeted tissue for prediction
   B. Total RNA and cDNA
   C. Prediction of Long-Term Post-Treatment Results
VI. Discriminant Analysis to Build the Prediction Model
VII. Optional Implementation Details, Examples, and Test Results
   A. Methods: Profiling by Microarray
     1. Microarray
     2. RNA extraction
     3. Labeling of cDNA probes
     4. Array Hybridization and Image Processing
   B. Data Analysis Using Discriminant Analysis
     1. Fisher's linear discriminant analysis
     2. K-nearest neighbor
   C. Examples
     1. Prediction of Radiotherapy Efficacy on Cervical Cancer
     2. Colorectal Cancer
     3. Ovarian Cancer
     4. In-Vitro Fertilization
   D. Sample Size
VIII. Computer Implementation
IX. Conclusion I. Introduction The present invention is directed to a process which combines microarray chip analysis of a patient's tissue with discriminant analysis for predicting the efficacy of the patient's proposed treatment plan. The process analyzes and correlates biological profiles (e.g., genomic profiles, DNA profiles, RNA profiles, protein profiles) from many patients with various medical conditions (e.g., human conditions such as diseases or infertility) to the clinical outcome of their respective treatment. The invention provides a basis for tailoring specific and effective clinical treatments for a given patient.

The present invention correlates clinical patient tissue and clinical treatment response directly. The invention provides a direct relationship through mathematical modeling without the need for pathway information. The invention utilizes data obtained from the complex human physiological environment, which is in contrast to those used in the in vitro and in vivo studies. The invention also addresses more elaborate drug delivery methods and other modalities of treatment (e.g., radiotherapy, in vitro fertilization).

The present invention is premised, at least in part, on the concept that inter-individual variability in drug response is due to biological (e.g., genetic) differences. This is referred to herein as pharmacogenetics. This is particularly significant for some drugs, such as chemotherapy used in the treatment of cancer. Such genetic differences may affect the drug's pharmacokinetics (e.g., metabolism or transport) or pharmacodynamics (e.g., target or modulating enzymes). The advent of DNA microarray for expression profiling provides a useful platform for a biological profile (e.g., genome-wide) approach for identifying molecular signatures of medical conditions such as diseases, previously unrecognized disease subsets, and prognostic categories, pathways, targets, and compounds. (See, Pagliarulo, V., et al., "Role of genetic and expression profiling in pharmacogenomics: the changing face of patient management," Curr. Issues Mol. Biol. 4:101-110 (2002), incorporated herein by reference in its entirety). This allows for a more systematic study of cancer, for example. "Personalized Medicine" is discussed in, for example, Mancinelli, L., et al., "Pharmacogenomics: The Promise of personalized Medicine, AAPS PharmSci 2000; 2(1) article 4 (2002), incorporated herein by reference in its entirety.

II. A Process for Predicting Treatment Outcome

The present invention combines microarray analysis of human tissues or specimens and discriminant analysis to predict treatment outcome. FIG. 1 is process flowchart of an example process 100 for generating and using a model that predicts an individual's treatment outcome from a sampling of a group of patients' biological profiles. The process 100 includes a model generating process 102 and a treatment outcome prediction process 104. The model generating process 102 generates a prediction model. The goal of the model generating process 102 is to learn from known input data (historical data), and to generate a model that discriminates between different treatment outcomes. The treatment outcome prediction process 104 predicts the treatment outcome of a new tissue sample.

The model generating process 102 starts with task definition 106, where model generation parameters are defined. Parameters can include, without limitation, scope definition. Scope definition can include, without limitation, identification of a method of treatment (e.g., chemotherapy, immunotherapy, radiotherapy, or in vitro fertilization). In a drug treatment case, there may be many possible treatment options, so a specific drug or combination drugs can be selected for study. Other parametric factors can include a predicted target (i.e., immediate drug response or long-term effect), tissue type (e.g., primary tumor, metastases, serum), tissue representation (e.g., profiling by RNA, DNA, and protein), and/or the number of tissue sample size large enough to be representative of the patient population. Parameters can also include additional considerations for tissue collection (e.g., total RNA including both normal and tumor) and treatment response variables (e.g., CT scan result, CEA values).

In step 108, treatment results 130 are collected from patients. Treatment results 130 can be collected in a variety of ways. For example, and without limitation, treatment results can be collected through the use of questionnaires that treating physicians, oncologists, and/or patients answer. The questionnaires can be computer implemented, paper, or combinations thereof. Treatment results can be collected from a single institution or various institutions. Treatment results 130 can be collected locally and/or remotely by electronic means and/or conventional mail delivery means.

In step 110, tissue samples 132 are collected from the patients.

In step 112, after determining the tissue processing technology (e.g. cDNA microarray), the microarray experiment is carried out on the tissue samples 132.

The patients' tissue processing results (e.g. gene expression values), illustrated in FIG. 1 as biological profile data 134, from the microarray, and the corresponding clinical treatment outcome records (e.g. responsive, non-responsive), (illustrated in FIG. 1 as treatment results 130) are used as inputs in a discriminant data analysis, illustrated in FIG. 1 as step 114. The different treatment outcomes (treatment results 130) and their corresponding biological profile data 134 (e.g., genomic expressions) are analyzed to identify their differences. The optimal result is then used to build a treatment prediction model 136. Decisions described above are discussed in sections below.

The second part of the process, treatment outcome prediction process 104, uses the model 136 to predict a treatment outcome for a new patient. The process begins at step 116, collecting the same type of tissue sample 138 as in step 110 from the patient. In step 118, the patient tissue 138 is prepared and processed using the same or substantially similar method as in step 112 to generate new patient biological profile (e.g., genomic) values 140. In step 120, the new patient biological profile values 140 are inputted into the prediction model 136 and a prediction result 142 is returned.

Where multiple alternative treatments are contemplated, an additional model 136 is generated for each treatment. In other words, the model generation process 102 is repeated for each treatment, using treatment results 130 obtained from patients who have undergone the corresponding treatment. The biological profile data 140 from the new patient is then provided to each of the models 136. Alternatively, where a particular model 136 is generated from a different type of tissue, a new patient tissue sample 138 may be required.

The model(s) 136 can be generated from treatment results in the form of a positive/negative response and/or in the form of a graded scale response (e.g., on a scale of 0-1). Where the model(s) 136 are generated from treatment results in the form of positive/negative response, the output prediction results 142 will also be in the form of a positive/negative response. Alternatively, where the model(s) 136 are generated from treatment results in the form of a graded scale response, the output prediction results 142 will also be in the form of a graded scale response. Where multiple treatments are under consideration, graded scale responses 142 can be used to select a preferred treatment from multiple positive treatments.

Each drug has a different mechanism of action. This intrinsic difference makes it difficult to relate drug activity to gene expression. As a result, it is possible that one specific procedure can be successful in predicting drug response, while unable to correctly predict the activity of other drugs or types of treatments. For example, single drug treatment and combination treatment are quite different; therefore, a procedure able to predict single drug treatment response may fail to predict the response for a combination of drugs. Different drug schedules also result in vastly different efficacy, and a procedure that predicts one particular drug delivery method (e.g., bolus) may not work under another scheduling (e.g., protracted). (See, Lévi F, et al. "A phase I-II trial of five-day continuous intra-venous infusion of 5-fluorouracil delivered at circadian rhythm modulated rate in patients with metastatic colorectal cancer," J Infus Chemother; 5:153-158 (1995), incorporated herein by reference in its entirety). Through careful selection of sample cases in diversified situations, we demonstrate that the invention is consistently useful in its ability to produce accurate prediction models.

This invention exhibits the abilities to predict the efficacy of a single drug, a combination of drugs, and other medical treatment options (e.g., radiotherapy, in vitro fertilization), thereby giving definitive results for the diagnosis and treatment of various medical conditions. The invention is applicable for predicting treatment response for many human diseases that require physical, biological, or chemical intervention.

III. Example Commercial Applications

In addition to predicting treatment outcomes for patients, the invention is applicable in a variety of other applications. For example, and without limitation, an example of a commercial application is to assist the development of cancer treatment plans. The prediction model ranks the response of available treatments, which could be used to rationally design a treatment plan.

Another application is helping to design new clinical drug trials. Many drugs fail during trials despite positive results in clinical testing. Sometimes, this is not because the drug fails to be beneficial, but because the efficacy rate is not high enough or the side effects are too severe. This invention addresses these issues by identifying patients who will benefit most from the drug and experience the least amount of side effects. For example, during phases I and II of clinical trials, patients' tissues could be preserved and the clinical treatment results recorded at the end of phase II. The tissue and clinical treatment results could then be used to generate a predictive model. The model could then be included during the phase III clinical trial.

Another application is the identification of potential preclinical trials. A prediction model can be built from an initial clinical trial. The model can then be used to decide what other diseases could be targeted with this drug. For example, after the clinical trial of a new colon cancer drug has been carried out, its data can be used to build a prediction model. The new model can then be used to test other tumors (e.g., ovarian, breast cancers) to select the best candidates for another clinical trial.

IV. Comparisons with Other Approaches on the Prediction of Treatment Outcome A. Top-Down Approach Versus Conventional Bottom-Up Approach In general, the relationship between gene expression and clinical treatment efficacy is very complex. To fully understand pharmacogenomics, a systems biology approach would have to be applied to study the interaction of the genome with its environment. Most studies begin by looking for marker gene(s). Biochemical pathways are then explored to understand the system of biological networks. There can be a large number of branches and feedback loops in the pathway network. In theory, one would need to analyze each gene and determine all the binding and reaction constants for each pathway and loop. Additional factors would also need to be accounted for in order to make a clinical model more realistic, such as cell volume and localization of proteins. This approach can be rather complex when predicting a combination drug or a combination modality treatment. Many additional pharmacological considerations would also have to be addressed in this model, such as the sequence of drugs delivered and the rate of drug delivery.

This is a classical reductionist approach, of studying an individual element to gain a gradual understanding of an entire system; i.e., a bottom-up approach. There are many benefits to using this method. New drug discovery will clearly benefit from pathway studies. The understanding of a whole system is the ultimate goal of pharmacogenomics. It is the main reason to establish the Pharmacogenetics Research Network and Knowledge Base consortium (PharmGKB). The Pharmacogenetics Knowledge Base (PharmGKB) is financially supported by grants from the National Institute of General Medical Sciences (NIGMS), Human Genome Research Institute (NHGRI) and National Library of Medicine (NLM) within the National Institutes of Health (NIH) and the Pharmacogenetics Research Network and Stanford University's Children's Health Initiative. This database will be used to study how human genetic polymorphism contribute to observed variations in therapeutic drug responses. PharmGKB's complicated database designs, which will be used by researchers to exchange study results, emphasize the complexity of the bottom-up approach. (See, Oliver, D. et al, "Ontology Development for a Pharmacogenetics Knowledge Base," Pac. Symp. Biocomput. 65-76 (2002), incorporated herein by reference in its entirety).

Thus, a great deal of resources and time are needed to carefully study these relationships, pathways, and networks. Currently, the studies are limited to simpler organisms, such as yeast (See, Ldeker, T., et al., "Integrated Genomic and Proteomic Analyses of a Systematically Perturbed Metabolic Network," Science, 292, 929-934 (2001), incorporated herein by reference in its entirety), and cell lines. (See, Butte, A. J., et al., "Discovering Functional Relationships Between RNA Expression and Chemotherapeutic Susceptibility Using Relevance Networks," Proc. Natl. Acad. Sci. USA 97, 12182-12186 (2000), incorporated herein by reference in its entirety). Even in these cases, the results show evidence of complicated networks. This bottom-up approach is also the basis of current patents on drug efficacy (e.g., U.S. Pat. No. 6,218,122 or U.S. Pat. No. 6,222,093, incorporated herein by reference in their entireties). These patents use in vitro experimentation to study pathways and predict drug response. So far, this approach is still in its infancy. The hope is that one day there will be enough knowledge to build a model to assist in the prediction of drug response.

The bottom-up approach of analyzing all relevant biological pathways is still in its early stages. It will be a long time before a prediction model can be built using this method. However, this invention hypothesizes that pathway information is not necessary for predicting treatment efficacy.

The present invention relates microarray expression profiles to clinical results directly. Usually, for closely related cause-and-effect events, one expects a statistical model can be built to correlate these two factors. However, this is not true for the current situation, as there are many steps between gene expression and treatment outcome. Besides, a clinical treatment response in humans is based on many other factors. Thus, the success of this top-down approach is a major concept of this invention.

B. Sample Patient to Form Prediction Model

Figure 2:
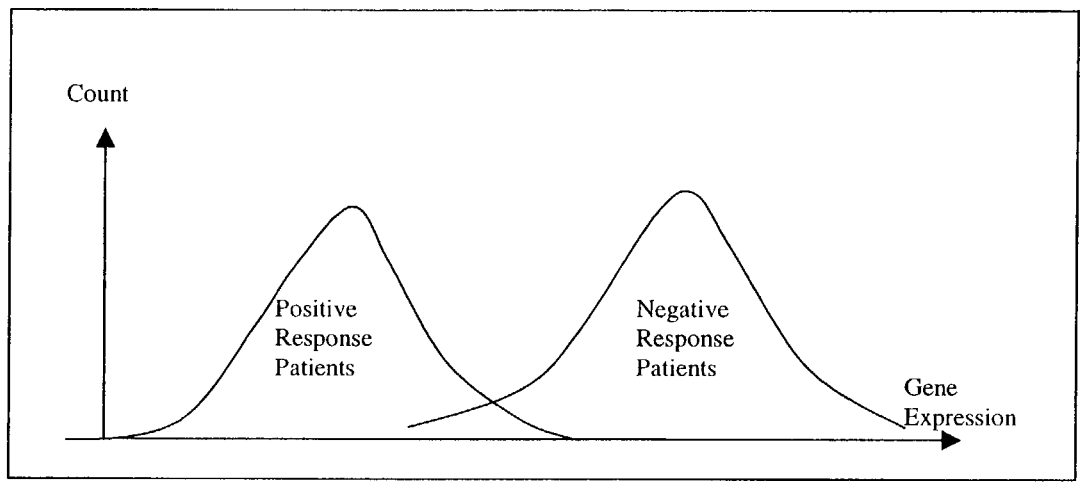
FIG. 2 illustrates an example of a separated gene distribution.

In a typical bottom-up approach, detailed information (e.g., pathways) provides the basis for building a model for drug efficacy prediction. In a top-down approach, this information may not be available. The present invention is based on sampling patients to form a statistical model. The supposition is that there is enough separation of expression profiles between patients in different clinical groups to provide a prediction model, despite the complex relationship between gene expression and clinical treatment outcome. In theory, the patient's gene profile distribution can be very complicated. The use of the right analytical tools is needed to correctly separate a patient population. FIG. 2 is a simplified example of this concept of separation. An actual distribution may different from the curve shown.

In FIG. 2, patients show two different clinical outcomes after a treatment. Each curve encloses a group of patients having similar outcomes. The separation of the distribution then allows for prediction of various clinical results.

V. Biological Profiles

A. Use a Patient's Non-Targeted Tissue for Prediction

A major difficulty in predicting treatment response for an individual patient is that of creating an actual human body environment. We propose that a patient's tissue is the best recorder of the patient's internal system, and a complete genome (or proteome) expression of the tissue would represent his/her true, in-vivo state.

In some bottom-up studies, a patient's tissue is used in an in vitro or in vivo experiment. In these experiments, the tissues respond to a simulated environment, which is different from the patient's original, internal environment. The present invention does not subject the patient's tissue to these experiments. Instead, the biological profile (e.g., gene expression results), represent the original in vivo state. This is an advantage of using the top-down approach.

In the top-down approach of the present invention, one still needs to decide what kind of tissue to use. One option is to use the tissue targeted for treatment; i.e., a primary tissue if the treatment is intended for primary tissue, and a metastatic tumor if the treatment target is metastases. However, target tissue may not be available. Even if a target tissue is available, it may not be desirable to use it. For example, even if a sample of metastases is available, there can be several variances of metastatic tumor in the same patients. So, one cannot always get the necessary tissue.

Often, primary tissue is not available. For example, it is well known that primary tumor cells undergo many mutational steps to become metastatic, resulting in a vastly different cell profile. In accordance with the present invention, however, a non-targeted tissue (e.g. primary tissue, granulosa cell) can be successfully used to predict targeted tissue (e.g. metastatic tumor, ovary) response to the treatment.

B. Total RNA and cDNA

The present invention can be implemented with one or more of a variety of types of biological profile information including, without limitation, genetic profile information, RNA profile information, DNA profile information, and protein profile information.

This invention can be implemented with RNA and/or DNA profile information taken from tissue samples containing mixed cell populations. A pure cancerous cell population is often preferable, but test results show that a homogeneous tissue specimen is not necessary for treatment prediction.

Tissue selection may depend, at least in part, on a selected microarray technology. Although microarrays have been successfully used, as described in published papers, probe design and processing still need improvement. This invention was tested with classic cDNA-based microarray to demonstrate its ability to predict treatment response. Future improvement of microarray processing will further enhance the prediction power of this invention.

C. Prediction of Long-Term Post-Treatment Results

Usually, a study of drug response is directed to the immediate result following treatment. However, long-term efficacy is another important factor in clinical treatment of diseases. In some cases, a cancer patient with complete response to a treatment can relapse after a period of time (e.g., two years). A method that can accurately predict relapse post-treatment would allow for a more timely intervention.

Since cancerous cells change continuously, the cumulative changes following a delay (e.g. up to and beyond 2 years) can be substantial. This situation can be further complicated by the use of primary tumor tissue for predicting long-term treatment response of metastatic tumors. The present invention can successfully predict a long-term response.

VI. Discriminant Analysis to Build the Prediction Model

The present invention uses a discriminant analysis to build models for predicting a patient's treatment outcome. For example, the invention can combine DNA microarray processing and discriminant analysis to build models for predicting each patient's individual treatment outcome.

This invention uses a class of data analysis methodology called "discriminant analysis", or "supervised clustering", (commonly used in the pattern recognition field) to analyze the biological profiles. Examples of discriminant analysis methods are the Linear Discriminant Method, Maximum Likelihood Method, K-Nearest Neighborhood Method, Neural Network, and Hidden Markov Method. This class of methods is different from un-supervised clustering methods commonly used in today's microarray data analysis, such as Hierarchical clustering, K-means clustering, and Self-Organized Map (SOM).

An un-supervised clustering analysis is a one-input (gene expression) and one-output (grouped samples or genes) method. Since there is no additional input/information needed to guide the grouping process, it is up to the user to select implementation details (e.g., the distance metrics), judge the soundness of the result, and interpret its meaning. This method is best used for "new class discovery".

While the unsupervised method is a single-step process, discriminant analysis/supervised clustering is a two-step process consisting of training and testing. The training step requires two inputs (e.g., gene expression and clinical outcome) and generates one output based on analyzing the relationship between the two inputs. The additional input of clinical outcome dictates the analytical process. The grouping information among the patients is known from the clinical observation. Thus, the purpose of training is not to group patients as in unsupervised clustering, but to solve a problem of "how" to separate groups through gene expression. The knowledge gained from the training is then used to build a model for "class prediction." During the testing step, information from other patients not used in the training process is used to test the performance of the model and determine its accuracy.

VII. Optional Implementation Details, Examples, and Test Results

Drug efficacy depends upon many factors, such as the pharmacodynamics and pharmacokinetics of the drugs used in therapy. Because of these many considerations, examples provided herein are designed to test diversified conditions using different treatment regimens on different diseases. The examples herein demonstrate the ability to predict different clinical observations: short-term treatment, long-term treatment, and different treatment modalities (e.g., radiotherapy, chemotherapy and in vitro fertilization). A prediction of chemotherapy response immediately after the end of the treatment cycle is an example test of short-term response. A prediction pertaining to relapse following a successful, complete response to chemotherapy is an example test of long-term response. The more difficult combination drug regimens are also used to illustrate the invention instead of the simpler single-drug regimens. The goal of the following example is to establish a generally successful methodology for a variety of cases.

A. METHODS

Profiling by Microarray

Expression profiling by DNA microarrays is continuously improving. (See, Heller M J. "DNA microarray technology: devices, systems, and applications," Annu. Rev. Biomed. Eng. 4:129-153 (2002); Chicurel, M. E., and Dalma-Weiszhausz, D. D., "Microarrays in pharmacogenomics—advances and future promise," Pharmacogenomics, 3:589-601 (2002); incorporated herein by reference in their entireties). However, to demonstrate this invention, a CDNA microarray is used. More advanced microarray techniques in the future may result in better performance using this invention.

cDNA microarrays printed on nylon filter were used. The RNA samples were reverse-transcribed and labeled using [$^{33}$P]dNTP. The reproducibility of this approach in using microarray printed on nylon membrane is akin to a Northern hybridization experiment.

1. Microarray

The example microarrays were produced using an Omni-Grid high throughput arrayer from GeneMachines. These arrays, printed on 3×8 in nylon membranes, contained approximately 11,000 DNA elements, corresponding to substantially all human transcripts with known function in the GenBank database (approximately 7,000) and some anonymous ESTs (>3,000).

2. RNA Extraction

Figure 3:
FIG. 3 is a photograph of a custom-made staple gun for pulverizing frozen tissue.

For this experiment, total RNA was isolated from tumor tissues consisting of at least 50% cancerous cells. In some cases, RNA was extracted by a hospital cancer center, suspended in ethanol, and shipped to the test center via express mail for analysis. Otherwise, frozen tissues were received packaged in dry ice. To pulverize the frozen tissue more effectively, a custom-made staple gun 300 (FIG. 3), fitted with a spring-loaded piston and a stainless steel holder was used. RNA of relatively high yield and good quality were routinely recovered by this procedure.

Figure 4:
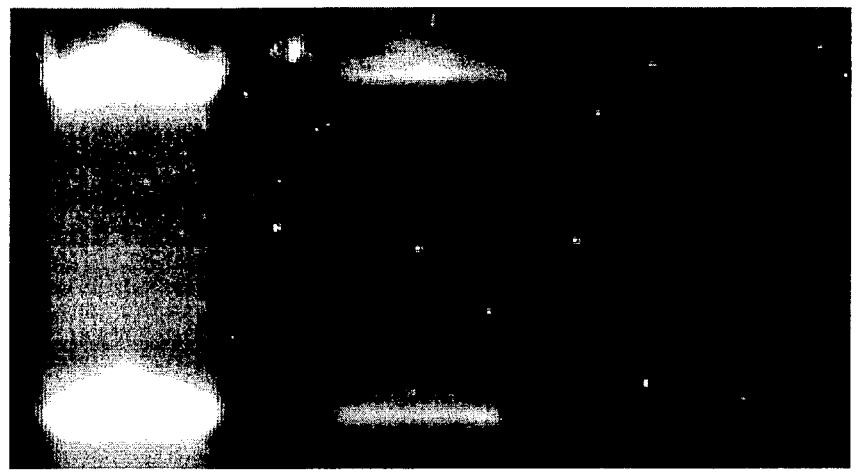
FIG. 4 is an example illustration of RNA examined by gel electrophoresis.

The samples were handled using standardized protocols to ensure minimal fluctuation in experimental conditions. RNA was isolated using an RNeasy Kit from Qiagen. Approximately 5 mg of pulverized tissue was homogenized in the RNA extraction reagent with a homogenizer (Dounce homogenizer). RNA from the homogenate tissue samples was then purified using mini-columns from the RNeasy Kit. Integrity of the isolated RNA was examined by gel electrophoresis to verify the quality of the 18S and 28S ribosomal RNA stained with molecular probes from SyberGold (FIG. 4). Stained RNA was detected by scanning with a phosphorimager. The high sensitivity of SyberGold enabled the use of as little as 1 ng of total RNA to validate the quality of the isolated RNA, which was advantageous when the amount of RNA samples was limited.

3. Labeling of cDNA Probes cDNA probes were synthesized from isolated total RNA with $^{33}$P-dCTP by oligo-dT-primed polymerization using Superscript II reverse transcriptase (Gibco/BRL). A typical labeling reaction using $^{33}$P-dCTP is shown in Table 1.

TABLE 1

Example of a labeling reaction using $^{33}$P-dCTP.

| Component | Volume (μl) |
|---|---|
| 5X first strand buffer | 6 |
| Oligo-dT$_{12\text{-}18}$ (500 μg/mL) | 2 |
| 10X low-dT dNTP mix | 1.5 |
| $^{33}$P-dCTP | 5 |
| 0.1 M DTT | 1 |
| 5 μg total RNA | 8 |
| SuperScript II RNAse H$^-$ Reverse Transcriptase | 1.5 |

4. Array Hybridization and Image Processing

The $^{33}$P-dCTP-labeled probes were hybridized to the filter arrays overnight. Washes were then conducted with 2×SSC/0.2% SDS (at 50° C. for 20 minutes) twice and 0.5×SSC/1% SDS (at 65° C. for 15 minutes) once. The washed filters were exposed to a phosphorimaging screen for 24 hours and then scanned on a Typhoon Phosphimager (FIG. 5) from Molecular Dynamics.

The scanned images were processed using Imagene (Biodiscovery) to extract each individual spot's intensity. These values were outputted as tab-delimited files, which were used in the discriminant/supervised clustering analysis.

Figure 5:
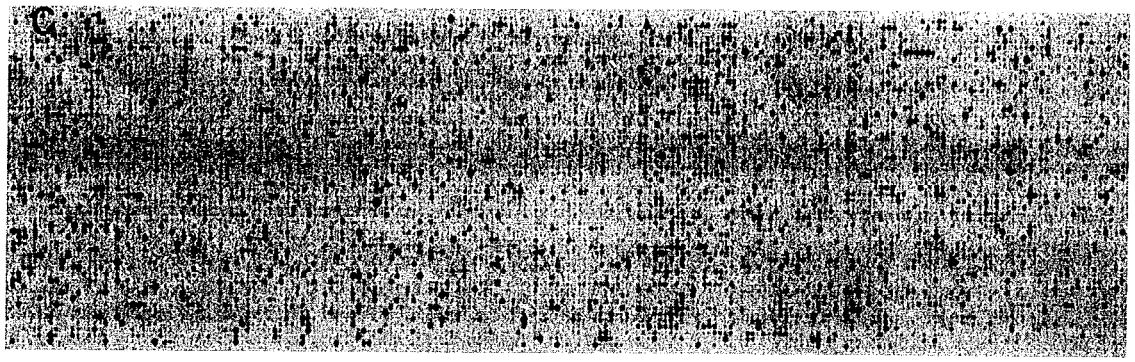
FIG. 5 is an example image produced by scanning a microarray.

In FIG. 5, a 10K human filter array is hybridized with probes labeled with 5 μg of total RNA isolated from cervical cancer tissues. The filter array is washed and exposed to a phosphorimage screen and then scanned with a phosphorimager.

B. DATA ANALYSIS USING DISCRIMINANT ANALYSIS

Microarray data analyses belong to one of two types of data classification. In the first category, the goal of the task is to explore the existence of clusters or classes in the data. The resulting grouping information is then used to perform other detailed analyses. In the second category, the class information is already known; the goal is to learn the differences between the classes, then use the knowledge to build a model. The model can be used to classify new data from an unknown class. The first category is called unsupervised learning/clustering or simply clustering. The latter is a supervised learning/clustering, also called discriminant analysis or pattern recognition in the literature.

Supervised learning assumes that there is someone (the supervisor) who can classify the data correctly. The knowledge required to build the prediction model can be provided directly by the supervisor or be learned by statistical inference of the data. Our data analysis derives this knowledge through statistical inference, and our supervisors are the clinicians who classify the patient responses after treatment but do not know how to differentiate between the different classes. This supervisor's classification and the microarray expression profile from the patient's tumor are the two inputs for our analysis.

The supervised learning methods have three basic approaches: linear discriminant analysis, probability density estimation, and decision-tree/rule-based methods. Decision-tree, or rule-based, methods have been shown to be successful in some phenotype data analysis (See, MALIN, B. A., SWEENEY, L. A., "Inferring genotype from clinical phenotype through a knowledge based algorithm," *Pacific Symposium on Biocomputing* 2002 (2000), incorporated herein by reference in its entirety), but are not as suitable for the analysis of the data described herein. This study will therefore use the first two methods. Examples of linear discriminant include classical Fisher's linear discriminant analysis, logistic discriminants, quadratic discriminants, support vector machines, (Brown, M. P. S., et al., "Knowledge based Analysis of Microarray Gene Expression Data by Using Support Vector Machines," Proc. Natl. Acad. Sci. USA 97, 262-267 (2000), incorporated herein by reference in its entirety), and perception networks. Examples of probability estimation methods include K-nearest-neighbors, Naïve Bayes, and multiple-leveled neural net (i.e., non-perceptron network).

In choosing a method for classification, unless the problem has been well-studied or the underlying structure is known, one usually needs to try as many different methods and approaches as possible. The assumption is that every set of data contains different sets of hidden structures. It is preferred not to predict the performance of each approach until many sets of data have been studied extensively.

1. Fisher's Linear Discriminant Analysis

Fisher's linear discriminant analysis (FLDA) is an empirical method using least square distances for classification. The goal is to choose an optimal hyperplane in the feature space to separate the known classes.

In the example, the goal is to classify tissues into two classes (i.e., sensitive vs. resistant). The feature space is defined by the genes used in the microarray. Every tissue sample is a point in this space. The FLDA classification finds an optimal line in this feature space to separate the two classes. This optimal line has the following property: if all tissue points are projected onto this line, the two groups of tissues (sensitive and resistant) will be most widely separated.

It can be shown that finding the optimal line is similar to finding the optimal ratio between within-group scatter and between-group scatter.

For each tissue sample, there is a gene expression vector X; the projection vector P will project X onto a line in the feature space with a scalar value Y.

$$Y = P^T X$$

Let tissues in group 1 have gene expression vector $X_1$. They have mean value of $\overline{X}_1$ and the variance among the projected values (i.e., $Y_1$) in group 1 is $S_1^2$. Similarly, the tissues in group 2 have gene expression vector $X_2$ with mean value $\overline{X}_2$ and variance $S_2^2$. So FLDA projects all gene vectors onto a line with an objective function J(P) and finds the largest value of J(P) among all possible projections P.

$$J(P) = |P^T \overline{X}_1 - P^T \overline{X}_2|^2 / (S_1^2 + S_2^2)$$

The numerator is the distance of separation between group 1 and group 2, and the denominator is the variance of these two groups. The variances are used to normalize/re-scale the distance separation, so J(P) can be compared among different projection vectors P.

The above equation can be further written as:

$$J(P)=P^T S_B P / P^T S_W P$$

where $S_B$ is the between-group scatter matrix, and $S_W$ is the within-group scatter matrix:

$$S_B = (\overline{X}_1 - \overline{X}_2)(\overline{X}_1 - \overline{X}_2)^T$$

$$S_W = \sum_1 (X_1 - \overline{X}_1)(X_1 - \overline{X}_1)^T + \sum_1 (X_2 - \overline{X}_2)(X_2 - \overline{X}_2)^T$$

The optimal value of J(P) can be determined by solving an eigenvalue problem for matrix $S_W^{-1} S_B$.

FLDA generally performs well for unimodal, Gaussian distributions. For other kinds of distributions, FLDA may not perform effectively. Since we do not know the probability distribution of gene values and each treatment's response derives from very different probability distributions, the performance of FLDA is hard to predict.

2. K-Nearest Neighbor

The K-nearest neighbor (KNN) rule is a simple non-parametric classifier with no prior knowledge of the distributions. Traditionally, KNN determination uses the following three steps:

For an unknown sample x, identify the k nearest neighbors from all training vectors.

Out of these k samples, identify the number of samples that belong to each class/group.

Assign x to the class that has the maximum number of samples out of the k nearest neighbors identified in the first step.

This method can encounter a situation where there is more than one class that has the same maximum number of samples out of the KNN. Thus, a conflict resolution process is required.

To avoid the conflict resolution process, the above majority-vote algorithm has been modified and will be called the KNN average distance comparison algorithm for this data analysis. Here are the modified KNN steps:

For a test vector x, find KNN for each training class/group i.

For each class/group, add distances from x to KNN.

$$D_i = \sum_{j \in KNN} dist_{xj}$$

where $dist_{xj}$ is the distance between vector x and sample vector j.

Assign x to the group m which has the smallest summarized distance among all possible $D_i$ $$D_m = \min\{D_i\}$$

It is clear from the above-described procedure that KNN performance depends greatly on the definition of distance. Many different kinds of distance measurements are available. The most common choice is the Euclidean distance and the correlation of gene vectors. In our current study, a correlation-based distance is used.

For the two gene vectors $X_1$ and $X_2$, the distance between them is defined as:

$$Dist_{12} = 1 - \Sigma(X_1 - \overline{X}_1)(X_2 - \overline{X}_2) / (\sqrt{\Sigma(X_1 - \overline{X}_1)^2} \sqrt{\Sigma(X_2 - \overline{X}_2)^2})$$

where $\Sigma$ is the sum of the gene values.

Comparisons between FLDA and KNN show that FLDA is generally better at finding the overall-differences between group 1 and group 2, while KNN generally better estimates local probability density. The results from these two methods provide a baseline performance of current invention.

C. EXAMPLES

The invention establishes a general procedure to predict treatment response. Optimization was performed with several methods in the analysis of different diseases with varied treatment protocols and objectives (e.g., short-term response, long-term relapse). These studies have been selected to ensure a coverage of diverse data sets with different hidden structures. A particular discriminant method, which gives the best performance in one case, may not perform as well for another. This invention is not so much about determining the best method for a particular set of data but more about demonstrating the successful use of discriminant analysis in treatment prediction. To test different methods, one representative method from linear discriminant analysis and another representative method from the probability estimate method were used: Fisher's linear discriminant analysis (FLDA) and K-nearest neighbor (KNN), respectively.

Expression profiles were obtained from several different groups of patients and then correlated microarray expression data with clinical treatment response. In each study, the available microarray data were randomly divided into training samples and test samples. The training samples were used to build possible prediction models. Each model's performance was then tested using the remaining test samples. The best performance model was chosen to be the final result.

During the training sessions, the training set data and its clinical grouping information (e.g., resistance vs. sensitivity) were the inputs for the discriminant analysis. Gene expressions from different clinical groups were examined to develop a model for optimally distinguishing among them. The knowledge from the training was then used to build a model for further "class prediction". The test samples were used to verify the correctness of the model and to select the best performance model.

Often the model's predictive performance depended on the initial choice of how to divide the data into training and testing samples. This occurred more often in small data sets. To avoid this bias, the division process was randomized many times. Each time, all the patients' microarray data were randomly re-separated into training and testing sets, and the entire training and testing processes were repeated. The accuracy of the final prediction model was determined by averaging the performances of all these repetitions. The results are reported below.

Four sets of data were used to test the invention: colorectal, ovarian, and cervical cancers and in-vitro-fertilization. The microarray data were analyzed using discriminant analysis to predict treatment outcome in case.

1. Prediction of Radiotherapy Efficacy on Cervical Cancer

The first study examined the expression profiles of cervical cancer patients. Twenty-six grossly dissected primary tumors from cervical cancer patients were collected. The patients' characteristics are shown in Table 2. Thirteen patients were given radiotherapy as primary treatment for the cervical cancer. They were chosen for our analysis and stratified into two groups based on treatment outcome 24 months later, as recorded in clinical outcome: patients who, despite the treatment, died of the disease (DOD) and patients who were alive with no evidence of disease (NED) since end of treatment. The RT resistant group had a mean of 20.6 months survival time, while the RT sensitive group had a mean survival time of 64.1 months. All the patients in the radiotherapy resistant group have since died from the disease, whereas patients in the radiotherapy sensitive group were all alive at the time when this study was conducted.

TABLE 2

Patients' data (n = 26 patients).

| Characteristics | Number of patients | % |
|---|---|---|
| FIGO stage | | |
| IB | 11 | 42.4 |
| IIA | 8 | 30.8 |
| IIB | 5 | 19.2 |
| IIIB | 1 | 3.8 |
| IVA | 1 | 3.8 |
| Tumor grade | | |
| 1 | 3 | 11.5 |
| 2 | 16 | 61.5 |
| 3 | 7 | 27 |

TABLE 3

Patients' time of survival at the time of analysis.

| Patient | Time of Survival (months) | Average (months) |
|---|---|---|
| C348 | 22 | 20.6 |
| C567 | 15 | Resistant Group |
| C502 | 27 | |
| C496 | 10 | |
| C495 | 37 | |
| C523 | 13 | |
| C522 | 50 | 64.1 |
| C451 | 72 | Sensitive Group |
| C464 | 67 | |
| C555 | 39 | |
| C366 | 86 | |
| C437 | 74 | |
| C477 | 61 | |

Figure 6:
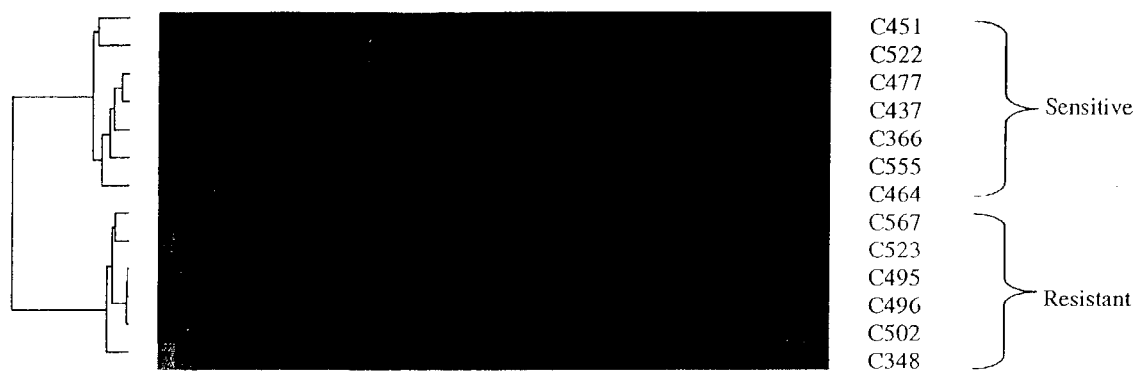
FIG. 6 is an example image generated for analysis of response to radiotherapy.

Discriminant analysis was used to analyze these 13 patients. The top 50 genes used in the prediction model are shown in FIG. 6, which correctly distinguished between the treatment outcomes as either radiotherapeutic-sensitive or radiotherapeutic-resistant. In FIG. 6, results from the most important genes that could be used in the classification of readioresistant and radiosensitive groups are displayed in a clustergram. Mean survival time (months) post-radiation treatment is shown in the table for the two groups of patients.

A patient with "no evidence of disease" two years after the treatment was defined as responsive, while any recurrence of cancer within two years was defined as resistant. During the training, one responsive patient and one resistant patient were randomly reserved as the test samples. The other 11 samples were used to build the model. To test whether the model was able to predict treatment response, the calibrated models were used to predict the outcome of the 2 reserved test samples. This test sample selection, data analysis, and testing were repeated 100 times. The average, randomized predication accuracy was 97%.

Some of the genes in the model represent a wide spectrum of cellular functions (Table 4) including genes with transcription, cell adhesion, and signal transduction functions.

TABLE 4

Genes differentially expressed between patients who responded (sensitive) or failed to respond (Resistant) to radiotherapy.

| Gene Name & Category | Accession # | Expression Ratio Sensitive/Resistant |
|---|---|---|
| Transcription Factors | | |
| T-box 19 | AI630980 | 0.43 |
| ZNF33A Zinc finger protein 33a (KOX 31) | N57658 | 0.47 |
| Serum response factor | AA487973 | 0.37 |
| Nuclear receptor co-repressor 1 | T99086 | 0.46 |
| Cell Death | | |
| Caspase 8 | AA448468 | 0.36 |
| Weakly similar to neuronal thread protein | N55563 | 0.45 |
| Programmed cell death 4 | R26827 | 0.45 |
| Actin-associated and cytoskeletal proteins | | |
| Highly similar to kininogen L | H69834 | 0.44 |
| KIAA0220 protein, actin cytoskeleton organization | R91822 | 0.38 |
| KIAA0336 gene product, similar to mouse myosin heavy chain | R00035 | 0.40 |
| KIAA0514 gene product, proline-rich actin-binding protein family | AI139146 | 0.48 |
| KIAA0966 protein, similar to SAC1, suppressor of actin mutations 1 homolog | R69354 | 0.43 |
| Ras family of proteins | | |
| N-ethylmaleimide-sensitive factor | H38086 | 0.35 |
| RAB7 | AI202933 | 0.42 |
| Similar to mouse putative Rho/Rac GEF | AI042352 | 0.39 |

2. Colorectal Cancer

Treatment of colorectal cancer was analyzed in our second study. The goal was to predict immediate chemotherapeutic response (i.e., assessing chemotherapy response immediately after treatment). The treatment protocol in this study was a combination of 5FU, Leucovorin, and CPT11 (Irinotecan) given every two weeks. The response was assessed every 4 cycles by CT scans and changes in CEA values. Ten patient samples were included in the study. The CT results were used to separate patients into responsive and resistant groups. Three partial response patients were assigned to the responsive group and two progressive patients were assigned to the resistant group. The 5 stable-disease patients determined by CT scan were further sorted into sensitive and resistant groups based on the changes in CEA levels during the treatment. All patients who had a 50% reduction in their CEA levels were assigned to the sensitive group, and the remainder to the resistant group. Because patients with stable disease were included in our analysis, the differences between the two groups were much smaller than without them. As this was the prediction of a combination drug regimen, there were possibly more factors that governed drug efficacy than those in a single drug treatment analysis. However, prediction accuracy of this test was found to be approximately 83%.

3. Ovarian Cancer

The third study is ovarian cancer treatment. Many patient underwent exploratory laparotomy with bilateral salpingo-oophorectomy, hysterectomy, and infracolic omentectomy and maximal tumor debulking as part of her treatment for ovarian cancer. All of the patients were then treated with postoperative platinum-based regimen chemotherapy (i.e., Cisplatin or Carboplatin, plus Cyclophosphamide or Taxol). Immediately after treatment, some patients were in a state of "no disease detectable". Out of 29 ovarian cancer samples, 8 stage III/IV cases had been treated with the drugs mentioned above and were in "no disease detectable" state after the treatment. While four of these patients remained disease-free (no evidence of disease) two years after the end of treatment, four have experienced clinical relapse. Our goal was to link microarray data to the relapse. Since the microarray data used in this test were taken from the initial surgery, there was a very long delay between the time the tissue was taken and the clinical outcome. The relationship between gene expression and outcome is very complicated, yet the prediction accuracy of this test was estimated at approximately 94%.

Finally, some of the ovarian cancer patients used Topoisomerase 1 inhibitor-based (e.g., Irinotecan or Topotecan) chemotherapeutic drugs after a relapse from the platinum-based treatment as a second line treatment. The prediction model constructed using the colorectal cancer patient data was able to predict the response correctly for ovarian cancer patients. This indicates that our model generated by one cancer can be used to predict the response in another cancer.

4. In-Vitro Fertilization

The invention was also tested on other medical conditions besides cancer. In this case, this study was to guide the in vitro fertilization (IVF) procedure. Eighteen women with 9 normal and 9 diminished ovarian reserves were included in this study. All patients were given gonadotropin stimulation in preparation for IVF with granulosa cells isolated at the time of follicular aspiration. The gene expression of luteinized granulosa cells isolated from women and the clinical information about their normal or diminished ovarian reserve information were the inputs for the discriminant analysis. The resulting model gave a perfect prediction for a patient's ovarian reserve from the gene expression of her granulosa cells.

The examples given above include predictions of short-term chemotherapy response, long-term chemotherapy response, and response to other treatment modalities (e.g., radiotherapy, in vitro fertilization). In summary, the results demonstrate the ability to predict response across different diseases. The results further demonstrate the ability to use expression profiles by DNA microarray and discriminant computational analysis for predicting treatment responsiveness. These results imply that patients whose tissue expression profiles exhibit patterns of resistance should be given alternative modalities of treatment that may result in improved responsiveness or cure, thus personalizing treatment for individuals based on their gene expression patterns.

D. SAMPLE SIZE

In microarray data analysis, the number of data points in a biological profile sample (e.g., genes) included in the experiment is often much larger than the sample size. Because of the large number of data points in a biological profile sample, such as genes, in theory, a small number of samples can be fitted by gene expression stochastically. This concern was addressed to ensure the results of the studies were not random.

This study used supervised discriminant analysis. The main goal is to fit the expression profile to the observed clinical result. A correctly implemented analysis of clinical data should discover the true genetic cause from observed clinical differences. The analysis of randomized data would not find any real "causes".

To test the validity of the analysis, the results from the analysis were compared to randomized data sets. In order to create randomized data, each patient's sample was arbitrarily assigned to different groups (i.e., new groups were artificially created by mixing positive and negative samples).

In this study, these artificially created groups had a roughly equal number of true positive and negative samples in each group. These groups were then subjected to discriminant analysis to create models to discriminate one group from another. The resulting accuracy of these models of artificial data was compared to the performance of the true data. Since there are many ways to create these neutral (i.e. equal number of positive and negative members) artificial groups, the data were repeatedly created and analyzed many times (>30) to assess the performance of the random results. Table 5 summarizes the results.

TABLE 5

Prediction Accuracy (%).

| | Analysis of clinical data | | Analysis of randomly grouped data | | | |
|---|---|---|---|---|---|---|
| | | | Self included | | Self excluded | |
| | Self included | Self excluded | prediction accuracy | | prediction accuracy | |
| | prediction accuracy | prediction accuracy | Mean Value | Standard Deviation | Mean Value | Standard Deviation |
| Colorectal Cancer | 96.3 | 83.3 | 89.1 | 3.8 | 47.5 | 19.9 |
| Cervical Cancer | 99.4 | 96.0 | 91.9 | 1.6 | 52.2 | 9.8 |
| Ovarian Cancer | 98.5 | 94.0 | 86.9 | 5.1 | 47.4 | 20.6 |

For both analyses of clinical observation based data or random grouped data, two different results were reported in Table 5: self-included and self-excluded. A self-included result includes the test sample during the analysis; a self-excluded result does not include the test sample. The self-excluded analysis is usually the reported result. A comparison of these two results corroborates the validity of the analysis. For randomized data, the self-included prediction accuracy is quite good; but the self-excluded accuracy is much worse; i.e., the good results in self-included prediction fail when attempting to predict unknown sample. This indicates that grouping contains no real information. This is exactly what one expected for artificially created neutral groups. On the other hand, self-included and self-excluded results are quite close for true clinical data. This is an indication that the model from true data is extracting the true genetic cause of clinical difference. Thus, this model can predict new samples as indicated by the high accuracy of self-excluded accuracy.

The second validity indictor is to compare the self-excluded accuracy of true clinical data against randomized data. The results of true clinical data reported in this study are about 2 standard deviations better (i.e., they are 1.8 SD, 4.5 SD and 2.3 SD away) than the randomized results. This means the clinical data based results are not occurring accidentally. This further supports the validity of the reported results.

VIII. Computer Implementation

The present invention can be implemented in one or more computer systems capable of carrying out the functionality described herein. For example, and without limitation, the model generating process 102 (FIG. 1) and/or the treatment outcome prediction process 104 (FIG. 1), or portions thereof, can be implemented in a computer system. More specifically, the discriminant analysis procedure (step 114 in FIG. 1), the resultant model(s) 136, and/or the treatment prediction procedure (step 120 in FIG. 1), or portions thereof, can be implemented in a computer system.

Figure 7:
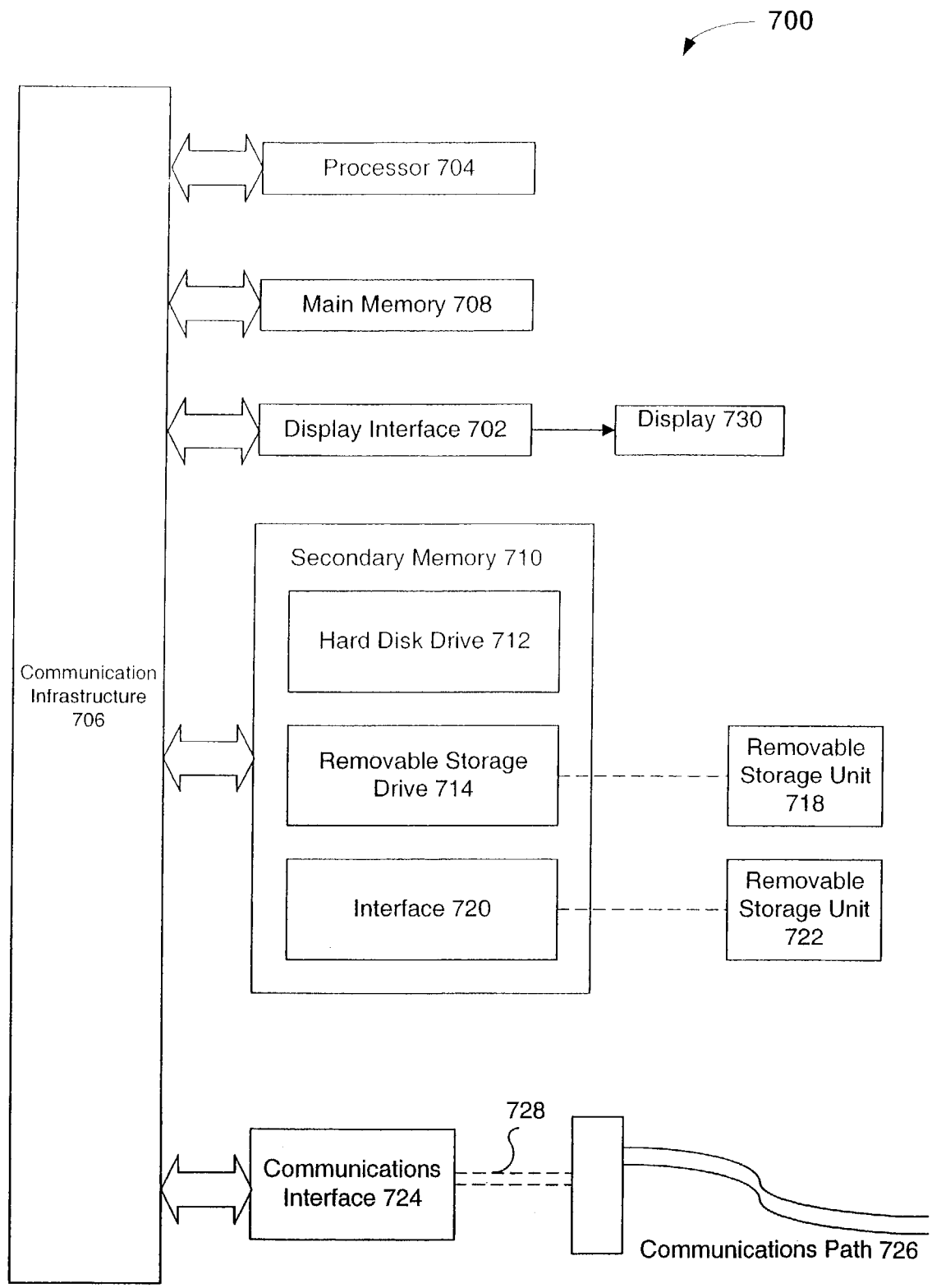
FIG. 7 is an example computer system in which the present invention can be implemented.

FIG. 7 illustrates an example computer system 700. Various software embodiments are described in terms of this example computer system 700. After reading this description, it will be apparent to a person skilled in the relevant art(s) how to implement the invention using other computer systems and/or computer architectures.

The example computer system 700 includes one or more processors 704. Processor 704 is connected to a communication infrastructure 702.

Computer system 700 also includes a main memory 708, preferably random access memory (RAM).

Computer system 700 can also include a secondary memory 710, which can include, for example, a hard disk drive 712 and/or a removable storage drive 714, which can be a floppy disk drive, a magnetic tape drive, an optical disk drive, etc. Removable storage drive 714 reads from and/or writes to a removable storage unit 718 in a well known manner. Removable storage unit 718, represents a floppy disk, magnetic tape, optical disk, etc. which is read by and written to by removable storage drive 714. Removable storage unit 718 includes a computer usable storage medium having stored therein computer software and/or data.

In alternative embodiments, secondary memory 710 can include other devices that allow computer programs or other instructions to be loaded into computer system 700. Such devices can include, for example, a removable storage unit 722 and an interface 720. Examples of such can include a program cartridge and cartridge interface (such as that found in video game devices), a removable memory chip (such as an EPROM, or PROM) and associated socket, and other removable storage units 722 and interfaces 720 that allow software and data to be transferred from the removable storage unit 722 to computer system 700.

Computer system 700 can also include a communications interface 724, which allows software and data to be transferred between computer system 700 and external devices. Examples of communications interface 724 include, but are not limited to a modem, a network interface (such as an Ethernet card), a communications port, a PCMCIA slot and card, etc. Software and data transferred via communications interface 724 are in the form of signals 728, which can be electronic, electromagnetic, optical or other signals capable of being received by communications interface 724. These signals 728 are provided to communications interface 724 via a signal path 726. Signal path 726 carries signals 728 and can be implemented using wire or cable, fiber optics, a phone line, a cellular phone link, an RF link and other communications channels.

In this document, the terms "computer program medium" and "computer usable medium" are used to generally refer to media such as removable storage unit 718, a hard disk installed in hard disk drive 712, and signals 728. These computer program products are means for providing software to computer system 700.

Computer programs (also called computer control logic) are stored in main memory 708 and/or secondary memory 710. Computer programs can also be received via communications interface 724. Such computer programs, when executed, enable the computer system 700 to perform the features of the present invention as discussed herein. In particular, the computer programs, when executed, enable the processor(s) 704 to perform the features of the present invention. Accordingly, such computer programs represent controllers of the computer system 700.

In an embodiment where the invention is implemented using software, the software can be stored in a computer program product and loaded into computer system 700 using removable storage drive 714, hard disk drive 712 or communications interface 724. The control logic (software), when executed by the processor(s) 704, causes the processor(s) 704 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

For example, and without limitation, in a computer implementation, the treatment results 130 and the biological profile data 134 are provided to the computer system 700, which then executes instructions for carrying out step 114, which results in a computer model 136. The new patient biological profile data 140 is then provided to the computer model 136 (in computer system 700 or in another computer system), which outputs prediction results 142.

IX. Conclusion

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like and combinations thereof.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A method for treating cancer, comprising obtaining the results of a correlation between patient biological profile information and the predictive information of post-treatment efficacy for a particular treatment selected from one or more treatments for a cancer, wherein the particular treatment comprises a drug treatment, wherein the correlation is obtained by:

i) identifying a group of patients who had the cancer and who underwent the particular treatment for the cancer's metastasis;
   ii) receiving multiple gene based pre-treatment biological profile information obtained through analysis of one or more of tissue and biological specimens obtained from the group of patients prior to the particular treatment;
   iii) receiving post-treatment efficacy information from the group of patients indicative of an impact of the particular treatment on the cancer's metastasis;

iv) performing a discriminant analysis-based pattern recognition process on the multiple gene based pre-treatment biological profile information and the post-treatment efficacy information, including identifying discriminating features of the multiple gene based pre-treatment biological profile information that correlate to different post treatment efficacies, and including generating a prediction model for the particular treatment that maps the multiple gene based pre-treatment biological profile information, using the discriminating features, to the corresponding different post treatment efficacies for the cancer's metastasis;

v) receiving multiple gene based pre-treatment biological profile information obtained through analysis of the one or more of tissue and biological specimens obtained from a new patient prior to the new patient receiving the particular treatment for the cancer; and vi) processing the new patient multiple gene based pre-treatment biological profile information according to the model, including using the discriminating features of the new patient multiple gene based pre-treatment biological profile information to predict an efficacy of the particular treatment for the new patient prior to the new patient receiving the particular treatment;

wherein the multiple gene based pre-treatment biologic profile information and the post-treatment efficacy information are received within a suitably programmed computer system, and wherein the discriminant analysis-based pattern recognition process is performed within the suitably programmed computer system, and treating the new patient with the particular treatment when the model predicts efficacy of the particular treatment for the new patient.

2. The method according to claim 1, further comprising generating the model to predict the efficacy of the particular treatment on a scale.

3. The method according to claim 1, further comprising: identifying one or more additional groups of patients who had the cancer and who underwent one or more corresponding other particular treatments; repeating, for each of the one or more additional groups of patients and the one or more corresponding other particular treatments, the receiving multiple gene based pre-treatment biological profile information, the receiving post-treatment efficacy outcome information, and the performing a discriminant analysis-based pattern recognition process, including generating one or more other corresponding prediction models for the one or more other particular treatments; and repeating the receiving new patient multiple gene based pre-treatment biological profile information and the processing of the new patient multiple gene based pre-treatment biological profile information for each of the one or more other predictions models to determine an efficacy of the one or more other particular treatments for the new patient prior to the new patient receiving any of the one or more other particular treatments.

4. The method according to claim 1, wherein the multiple gene based pre-treatment biological profile information comprises DNA profile information.

5. The method according to claim 1, wherein the multiple gene based pre-treatment biological profile information comprises RNA profile information.

6. The method according to claim 1, wherein the multiple gene based pre-treatment biological profile information comprises multiple protein profile information.

7. The method according to claim 1, wherein the multiple gene based pre-treatment biological profile information is embedded on a microarray.

8. The method according to claim 7, wherein the multiple gene based pre-treatment biological profile information is generated from a genomic analysis.

9. The method according to claim 1, wherein the receiving pre-treatment biological profile information from the group of patients comprises receiving the pre-treatment biological profile information from fewer than 100 patients.

10. The method according to claim 1, wherein the receiving pre-treatment biological profile information from the group of patients comprises receiving the pre-treatment biological profile information from greater than 100 patients.

11. The method according to claim 1, wherein the performing a discriminant analysis-based pattern recognition process comprises reducing the multiple gene based pre-treatment biological profile information to a sub-set of genes that account for a substantial portion of diversity.

12. The method according to claim 11, further comprising embedding a representation of the sub-set of genes on a microarray chip as part of the model.

13. The method according to claim 12, wherein the receiving pre-treatment biological profile information from a new patient comprises receiving genetic profile information from the new patient regarding only the sub-set of genes.

14. The method according to claim 11, wherein the receiving pre-treatment biological profile information from a new patient comprises receiving genetic profile information from the new patient regarding only the sub-set of genes.

15. The method according to claim 1, wherein the processing of the new patient pre-treatment biological profile information to predict the efficacy of the particular treatment for the new patient is performed within a suitably programmed computer system.

16. The method according to claim 1, further comprising using the model to predict efficacy of a first line treatment for a cancer patient.

17. The method according to claim 1, further comprising using the model to predict efficacy of a single drug treatment.

18. The method according to claim 1, further comprising using the model to predict efficacy of a multiple combination drug treatment for the cancer.

19. The method according to claim 1, further comprising using the model to predict efficacy of a first line single drug treatment.

20. The method according to claim 1, further comprising using the model to predict efficacy of a first line multiple combination drug treatment for the cancer.

21. The method according to claim 1, further comprising using the model to predict efficacy of a later-line drug treatment for the cancer.

22. The method according to claim 1, further comprising: receiving multiple gene based pre-treatment biological profile information obtained through analysis of the one or more of tissue and biological specimens obtained from a second new patient prior to the second new patient receiving the particular treatment for a second cancer; and processing the second new patient multiple gene based pre-treatment biological profile information according to the model, generated with respect to the first cancer of i) and never trained by the second cancer, including using the discriminating features of the second new patient multiple gene based pre-treatment biological profile information to predict an efficacy of the particular treatment for the second new patient with respect to the second cancer.

23. The method according to claim 22, wherein the first cancer of i) comprises colon cancer and the second cancer comprises ovarian cancer.

24. The method according to claim 22, wherein the first cancer of i) comprises a first type of tumor and the second cancer comprises a second type of tumor related to the first type of tumor.

25. The method according to claim 24, wherein the first type of tumor is primary tumor and the second type of tumor is a metastatic tumor.

26. The method according to claim 1, wherein the multiple gene based pre-treatment biological profile information comprises microarray expression profile information.

27. The method according to claim 26, wherein the microarray expression profile data is obtained from one or more of the following sources:
nucleic acid expression profiles; protein expression profiles; and single nucleotide polymorphisms.

28. The method according to claim 1, further comprising using the model for a deterministic treatment administration tool for personalized medical treatment.

29. The method according to claim 1, wherein the treatment efficacy information comprises objective features.

30. The method according to claim 1, wherein the pre-treatment biological profile information and the treatment efficacy information is received from patients who benefitted from a clinical trial of the treatment.

31. The method according to claim 30, further comprising submitting an application for approval of the particular treatment for use with new patients for whom the model outputs a favorable predicted treatment efficacy.

32. The method according to claim 1, wherein the performing a discriminant analysis-based pattern recognition process of part iv comprises:
dividing the biological profile information and the treatment efficacy information into a training sub-set and a testing sub-set;
performing the discriminant analysis-based pattern recognition process on the training sub-set; and
testing the resultant model with the testing sub-set.

33. The method according to claim 1, wherein the performing a discriminant analysis-based pattern recognition process comprises:
dividing the biological profile information and the post-treatment efficacy information into a training sub-set of biological profile information and post-treatment efficacy information and a testing sub-set of biological profile information and post-treatment efficacy information;
performing a plurality of different types of discriminant analysis-based pattern recognition processes on the training sub-set of biological profile information and treatment efficacy information, including generating a plurality of models that correlate between the training set of biological profile information and the training set of post-treatment efficacy information;
testing the plurality of models with the testing sub-set of biological profile information and treatment efficacy information; and
selecting the model that most accurately predicts the testing sub-set of treatment efficacy information from the testing sub-set of biological profile information.

34. The method according to claim 33, further comprising: selecting new testing sub-sets of biological profile information and treatment efficacy information;
repeating the performing a plurality of different types of discriminant analysis-based pattern recognition processes for the new sub-sets of biological profile information; and
averaging the results for each of the plurality of models;
wherein the selecting the model comprises selecting the model that most accurately predicts, on average, the testing sub-set of treatment efficacy information from the testing sub-set of biological profile information.

35. The method according to claim 1, wherein the multiple gene based pre-treatment biological profile information is obtained from targeted tissue samples.

36. The method according to claim 1, further comprising selecting a mode of treatment for the new patient based on the predicted treatment efficacy.

37. The method according to claim 1, wherein the performing a discriminant analysis-based pattern recognition process is performed without biological pathway information.

38. The method according to claim 1, further comprising: submitting an application for approval of the particular treatment for use with new patients for whom the model outputs a favorable predicted treatment efficacy.

39. The method according to claim 1, further comprising: analyzing the one or more of tissue and biological specimens of the group of patients to obtain the multiple gene based pre-treatment biological profile information regarding the group of patients.

40. The method according to claim 1, wherein the multiple gene based pre-treatment biological profile information comprises one or more of the following:
genetic profile information; DNA profile information;
RNA profile information; and multiple protein profile information.

41. The method of claim 1, wherein the efficacy information includes cell response information associated with tissue to which the particular treatment is targeted.

42. The method of claim 41, wherein the efficacy information includes tissue scan information.

43. The method of claim 41, wherein the efficacy information includes blood information.

44. The method of claim 1, further comprising:
classifying the multiple gene based pre-treatment biological profile information of the group of patients with respect to sensitivity of the patients to the treatment based on the efficacy information;
wherein the performing of the discriminant analysis-based pattern recognition process includes performing the discriminant analysis-based pattern recognition process on the multiple gene based pre-treatment biological profile information and classifications of sensitivity of the patients to the treatment, including,
identifying discriminating features of the multiple gene based pre-treatment biological profile information that correlate to different classifications of sensitivity, and
generating a prediction model for the particular treatment that maps the multiple gene based pre-treatment biological profile information, using the discriminating features, to the corresponding different classifications of sensitivity; and
wherein the processing of the new patient pre-treatment biological profile information includes using the discriminating features of the new patient multiple gene based pre-treatment biological profile information to identify a classification of sensitivity to the particular treatment for the new patient.

45. The method of claim 44, wherein the classifications of sensitivity include a sensitive classification and a resistive classification.

46. The method of claim 44, wherein the classifications of sensitivity include a sensitivity scale.

47. The method of claim 1, wherein the drug treatment is chemotherapy.

48. The method of claim 1, wherein the drug treatment is chemotherapy and the disease is colorectal cancer.

49. The method of claim 1, wherein the drug treatment is chemotherapy and the disease is ovarian cancer.

50. The method of claim 49, wherein the chemotherapy is platinum based chemotherapy.

51. A method for treating cervical cancer, comprising obtaining the results of a correlation between patient biological profile information and the predictive information of post-treatment efficacy for a radiotherapy treatment for cervical cancer, wherein the correlation is obtained by:
  i) identifying a group of patients who had the cervical cancer and who underwent the radiotherapy treatment for the cervical cancer;
  ii) receiving multiple gene based pre-treatment biological profile information obtained through analysis of one or more of tissue and biological specimens obtained by surgery from the group of patients prior to the radiotherapy treatment;
  iii) receiving post-treatment efficacy information from the group of patients indicative of an impact of the radiotherapy treatment;
  iv) performing a K-Nearest-Neighbor discriminant analysis-based pattern recognition process on the multiple gene based pre-treatment biological profile information and the post-treatment efficacy information, including identifying discriminating features of the multiple gene based pre-treatment biological profile information that correlate to different post treatment efficacies, and including generating a prediction model for the radiotherapy treatment that maps the multiple gene based pre-treatment biological profile information, using the discriminating features, to the corresponding different post treatment efficacies;
  v) receiving multiple gene based pre-treatment biological profile information obtained through analysis of the one or more of tissue and biological specimens obtained from a new patient prior to the new patient receiving the radiotherapy treatment for the cervical cancer; and
  vi) processing the new patient multiple gene based pre-treatment biological profile information according to the model, including using the discriminating features of the new patient multiple gene based pre-treatment biological profile information to predict an efficacy of the radiotherapy treatment for the new patient prior to the new patient receiving the radiotherapy treatment;
  wherein the multiple gene based pre-treatment biologic profile information and the post-treatment efficacy information are received within a suitably programmed computer system, and wherein the discriminant analysis-based pattern recognition process is performed within the suitably programmed computer system,
  and treating the new patient with the radiotherapy treatment when the model predicts efficacy of the radiotherapy treatment for the new patient.

52. A method for treating colorectal cancer, comprising obtaining the results of a correlation between patient biological profile information and the predictive information of post-treatment efficacy of the cancer's metastasis for a chemotherapy treatment for colorectal cancer comprising a combination of 5FU, leucovorin and CPT11, wherein the correlation is obtained by:
  i) identifying a group of patients who had the colorectal cancer and who underwent the chemotherapy treatment for the colorectal cancer's metastasis;
  ii) receiving multiple gene based pre-treatment biological profile information obtained through analysis of one or more of tissue and biological specimens obtained by surgery from the group of patients prior to the chemotherapy treatment;
  iii) receiving post-treatment efficacy information from the group of patients indicative of an impact of the chemotherapy treatment on the cancer's metastasis;
  iv) performing a K-Nearest-Neighbor discriminant analysis-based pattern recognition process on the multiple gene based pre-treatment biological profile information and the post-treatment efficacy information, including identifying discriminating features of the multiple gene based pre-treatment biological profile information that correlate to different post treatment efficacies, and including generating a prediction model for the chemotherapy treatment that maps the multiple gene based pre-treatment biological profile information, using the discriminating features, to the corresponding different post treatment efficacies for the cancer's metastasis;
  v) receiving multiple gene based pre-treatment biological profile information obtained through analysis of the one or more of tissue and biological specimens obtained from a new patient prior to the new patient receiving the chemotherapy treatment for the colorectal cancer; and
  vi) processing the new patient multiple gene based pre-treatment biological profile information according to the model, including using the discriminating features of the new patient multiple gene based pre-treatment biological profile information to predict an efficacy of the chemotherapy treatment for the new patient prior to the new patient receiving the chemotherapy treatment;
  wherein the multiple gene based pre-treatment biologic profile information and the post-treatment efficacy information are received within a suitably programmed computer system, and wherein the discriminant analysis-based pattern recognition process is performed within the suitably programmed computer system,
  and treating the new patient with the chemotherapy treatment when the model predicts efficacy of the chemotherapy treatment for the new patient.

53. A method for treating ovarian cancer, comprising obtaining the results of a correlation between patient biological profile information and the predictive information of post-treatment efficacy of the cancer's metastasis for a chemotherapy treatment for ovarian cancer comprising cisplatin or carboplatin, plus cyclophosphamide or taxol, wherein the correlation is obtained by:
  i) identifying a group of patients who had the ovarian cancer and who underwent the chemotherapy treatment for the ovarian cancer's metastasis;
  ii) receiving multiple gene based pre-treatment biological profile information obtained through analysis of one or more of tissue and biological specimens obtained by surgery from the group of patients prior to the chemotherapy treatment;
  iii) receiving post-treatment efficacy information from the group of patients indicative of an impact of the chemotherapy treatment on the cancer's metastasis;
  iv) performing a K-Nearest-Neighbor discriminant analysis-based pattern recognition process on the multiple gene based pre-treatment biological profile information and the post-treatment efficacy information, including identifying discriminating features of the multiple gene based pre-treatment biological profile information that correlate to different post treatment efficacies, and including generating a prediction model for the chemotherapy treatment that maps the multiple gene based pre-treatment biological profile information, using the discriminating features, to the corresponding different post treatment efficacies for the cancer's metastasis;

v) receiving multiple gene based pre-treatment biological profile information obtained through analysis of the one or more of tissue and biological specimens obtained from a new patient prior to the new patient receiving the chemotherapy treatment for the ovarian cancer; and vi) processing the new patient multiple gene based pre-treatment biological profile information according to the model, including using the discriminating features of the new patient multiple gene based pre-treatment biological profile information to predict an efficacy of the chemotherapy treatment for the new patient prior to the new patient receiving the chemotherapy treatment;

wherein the multiple gene based pre-treatment biologic profile information and the post-treatment efficacy information are received within a suitably programmed computer system, and wherein the discriminant analysis-based pattern recognition process is performed within the suitably programmed computer system, and treating the new patient with the chemotherapy treatment when the model predicts efficacy of the chemotherapy treatment for the new patient.

54. A method for treating cancer, comprising obtaining the results of a correlation between patient biological profile information and the predictive information of post-treatment efficacy for a particular treatment selected from one or more treatments for a cancer, wherein the particular treatment comprises a radiotherapy treatment, wherein the correlation is obtained by:

i) identifying a group of patients who had the cancer and who underwent the particular treatment for the cancer;

ii) receiving multiple gene based pre-treatment biological profile information obtained through analysis of one or more of tissue and biological specimens obtained from the group of patients prior to the particular treatment;

iii) receiving post-treatment efficacy information from the group of patients indicative of an impact of the particular treatment;

iv) performing a discriminant analysis-based pattern recognition process on the multiple gene based pre-treatment biological profile information and the post-treatment efficacy information, including identifying discriminating features of the multiple gene based pre-treatment biological profile information that correlate to different post treatment efficacies, and including generating a prediction model for the particular treatment that maps the multiple gene based pre-treatment biological profile information, using the discriminating features, to the corresponding different post treatment efficacies;

v) receiving multiple gene based pre-treatment biological profile information obtained through analysis of the one or more of tissue and biological specimens obtained from a new patient prior to the new patient receiving the particular treatment for the cancer; and vi) processing the new patient multiple gene based pre-treatment biological profile information according to the model, including using the discriminating features of the new patient multiple gene based pre-treatment biological profile information to predict an efficacy of the particular treatment for the new patient prior to the new patient receiving the particular treatment;

wherein the multiple gene based pre-treatment biologic profile information and the post-treatment efficacy information are received within a suitably programmed computer system, and wherein the discriminant analysis-based pattern recognition process is performed within the suitably programmed computer system, and treating the new patient with the particular treatment when the model predicts efficacy of the particular treatment for the new patient.

\* \* \* \* \*